United States Patent
Reddy et al.

(10) Patent No.: US 10,617,402 B2
(45) Date of Patent: Apr. 14, 2020

(54) MINIMALLY INVASIVE METHOD TO IMPLANT A SUBCUTANEOUS ELECTRODE

(71) Applicant: CAMERON HEALTH INC, St. Paul, MN (US)

(72) Inventors: G. Shantanu Reddy, Minneapolis, MN (US); Bruce A. Tockman, Scandia, MN (US)

(73) Assignee: CAMERON HEALTH, INC., St. Paul, MN (US)

( * ) Notice: Subject to any disclaimer, the term of this patent is extended or adjusted under 35 U.S.C. 154(b) by 476 days.

(21) Appl. No.: 15/208,707

(22) Filed: Jul. 13, 2016

(65) Prior Publication Data

US 2017/0020551 A1    Jan. 26, 2017

Related U.S. Application Data

(60) Provisional application No. 62/195,700, filed on Jul. 22, 2015.

(51) Int. Cl.
*A61B 17/32* (2006.01)
*A61N 1/05* (2006.01)
(Continued)

(52) U.S. Cl.
CPC .... *A61B 17/00234* (2013.01); *A61B 17/0218* (2013.01); *A61B 17/3468* (2013.01);
(Continued)

(58) Field of Classification Search
CPC ............ A61B 17/3468; A61B 17/3401; A61B 17/3415; A61B 2017/00331;
(Continued)

(56) References Cited

U.S. PATENT DOCUMENTS 3,902,501 A    9/1975   Citron et al.
4,437,475 A    3/1984   White
(Continued)

FOREIGN PATENT DOCUMENTS

JP    H0557863 B2    8/1993
WO    0174251 A2    10/2001
(Continued)

OTHER PUBLICATIONS

"Invitation to Pay Additional Fees and, Where Applicable, Protest Fee," mailed Oct. 5, 2016.
(Continued)

*Primary Examiner* — Kathleen S Holwerda
(74) *Attorney, Agent, or Firm* — Seager, Tufte & Wickhem LLP

(57) ABSTRACT

Methods and tool kits for implanting a lead subcutaneously. Examples include tool kits and methods for establishing first and second subcutaneous tunnels at an angle relative to one another to facilitate introduction of a lead to the subcutaneous space. In an example, a first insertion tool is used to establish a first subcutaneous tunnel, and a second insertion tool, with or without the use of a blunt dissector, sheath, guidewire, or steering mechanism, is used to initiate or form the second subcutaneous tunnel. Such methods and tool kits may reduce the number of incisions needed to implant a subcutaneous lead along a subcutaneous path having a curve therein.

17 Claims, 18 Drawing Sheets

(51) Int. Cl.
  *A61B 17/00* (2006.01)
  *A61N 1/39* (2006.01)
  *A61B 17/34* (2006.01)
  *A61B 17/02* (2006.01)
  *A61B 17/3201* (2006.01)
  *A61B 17/3205* (2006.01)

(52) U.S. Cl.
  CPC ......... *A61N 1/0504* (2013.01); *A61N 1/3956* (2013.01); *A61B 17/3201* (2013.01); *A61B 17/32053* (2013.01); *A61B 2017/003* (2013.01); *A61B 2017/0212* (2013.01); *A61B 2017/320044* (2013.01); *A61B 2017/320056* (2013.01); *A61B 2017/3454* (2013.01)

(58) Field of Classification Search
  CPC .......... A61B 17/00234; A61B 17/0218; A61B 17/3201; A61B 17/32053; A61N 1/05; A61N 1/0504; A61N 1/0551; A61N 1/3956
  USPC .................................................. 606/129, 185
  See application file for complete search history.

(56) References Cited

U.S. PATENT DOCUMENTS

| | | | |
|---|---|---|---|
| 5,105,826 A | 4/1992 | Smits et al. | |
| 5,746,722 A | 5/1998 | Pohndorf et al. | |
| 5,755,767 A | 5/1998 | Doan et al. | |
| 5,902,329 A | 5/1999 | Hoffmann et al. | |
| 6,136,021 A | 10/2000 | Tockman et al. | |
| 6,256,542 B1 | 7/2001 | Marshall | |
| 6,501,993 B2 | 12/2002 | Morgan et al. | |
| 6,647,292 B1 | 11/2003 | Bardy et al. | |
| 6,712,826 B2 | 4/2004 | Lui | |
| 6,721,597 B1 | 4/2004 | Bardy et al. | |
| 6,754,528 B2 | 6/2004 | Bardy et al. | |
| 6,934,589 B2 | 8/2005 | Sundquist et al. | |
| 7,090,682 B2 | 8/2006 | Sanders et al. | |
| 7,149,575 B2 | 12/2006 | Ostroff et al. | |
| 7,194,302 B2 | 3/2007 | Bardy et al. | |
| 7,218,970 B2 | 5/2007 | Ley et al. | |
| 7,218,971 B2 | 5/2007 | Heil, Jr. et al. | |
| 7,236,829 B1 | 6/2007 | Farazi et al. | |
| 7,248,921 B2 | 7/2007 | Palreddy et al. | |
| 7,376,458 B2 | 5/2008 | Palreddy et al. | |
| 7,392,085 B2 | 6/2008 | Warren et al. | |
| 7,463,933 B2 | 12/2008 | Wahlstrom et al. | |
| 7,477,935 B2 | 1/2009 | Palreddy et al. | |
| 7,499,758 B2 | 3/2009 | Cates et al. | |
| 7,623,909 B2 | 11/2009 | Sanghera et al. | |
| 7,623,913 B2 | 11/2009 | Phillips | |
| 7,655,014 B2 | 2/2010 | Ko et al. | |
| 7,890,191 B2 | 2/2011 | Rutten et al. | |
| 8,265,737 B2 | 9/2012 | Warren et al. | |
| 8,437,867 B2 | 5/2013 | Murney et al. | |
| 8,718,793 B2 | 5/2014 | O'Connor | |
| 8,744,555 B2 | 6/2014 | Allavatam et al. | |
| 9,149,637 B2 | 10/2015 | Warren et al. | |
| 2002/0049485 A1 | 4/2002 | Smits | |
| 2003/0074041 A1 | 4/2003 | Parry et al. | |
| 2004/0102804 A1 | 5/2004 | Chin | |
| 2004/0230274 A1 | 11/2004 | Heil et al. | |
| 2006/0122676 A1 | 6/2006 | Ko et al. | |
| 2006/0167503 A1 | 7/2006 | Warren et al. | |
| 2006/0247753 A1 | 11/2006 | Wenger et al. | |
| 2008/0046056 A1 | 2/2008 | O'Connor | |
| 2008/0196939 A1 | 8/2008 | Lubenow et al. | |
| 2009/0036944 A1 | 2/2009 | Fonte | |
| 2009/0187227 A1 | 7/2009 | Palreddy et al. | |
| 2009/0198295 A1 | 8/2009 | Dennis et al. | |
| 2009/0198296 A1 | 8/2009 | Sanghera et al. | |
| 2009/0228057 A1 | 9/2009 | Allavatam et al. | |
| 2009/0248054 A1 | 10/2009 | Sage et al. | |
| 2009/0276025 A1 | 11/2009 | Burnes et al. | |
| 2009/0312712 A1 | 12/2009 | Olson | |
| 2010/0030311 A1 | 2/2010 | Lazeroms et al. | |
| 2010/0152798 A1 | 6/2010 | Sanghera et al. | |
| 2010/0179562 A1* | 7/2010 | Linker ................. | A61N 1/0551 606/129 |
| 2011/0082516 A1 | 4/2011 | Kast et al. | |
| 2011/0245645 A1 | 10/2011 | Kenngott et al. | |
| 2012/0029335 A1* | 2/2012 | Sudam ..................... | A61N 1/05 600/374 |
| 2015/0133951 A1 | 5/2015 | Seifert et al. | |
| 2015/0133953 A1 | 5/2015 | Seifert et al. | |
| 2015/0209077 A1* | 7/2015 | Marshall ............ | A61B 17/3468 606/129 |
| 2015/0342627 A1* | 12/2015 | Thompson-Nauman ................... | A61N 1/05 606/129 |
| 2015/0343197 A1* | 12/2015 | Gardeski ................. | A61N 1/05 606/129 |

FOREIGN PATENT DOCUMENTS

| | | |
|---|---|---|
| WO | 2006062590 A1 | 6/2006 |
| WO | 2009117534 A2 | 9/2009 |
| WO | 2010083308 A1 | 7/2010 |

OTHER PUBLICATIONS

Darrat, Y. (May 11, 2018). B-PO05-034 / B-PO05-034—Single Incision Technique for Placement of Subcutaneous Implantable Cardioverter Defibrillators. Retrieved from http://abstractsonline.com/pp8/#!/4554/presentation/7501.

Lang et al., "Implantable Cardioverter Defibrillator Lead Technology: Improved Performance and Lower Defibrillation Thresholds," PACE, vol. 18, pp. 548-559m Pt II, Mar. 1995.

Haqqani et al., "Review—The Implantable Cardioverter-Defibrillator Lead: Principles, Progress, and Promises," PACE, vol. 32, pp. 1336-1353, Oct. 2009.

* cited by examiner

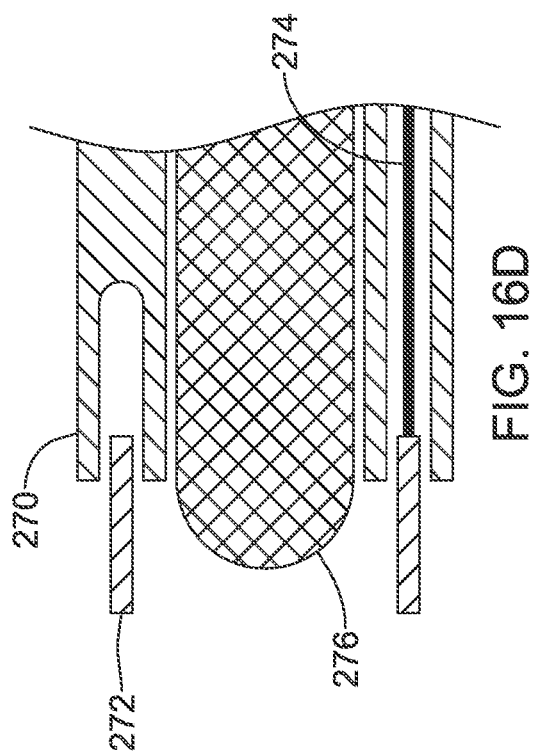
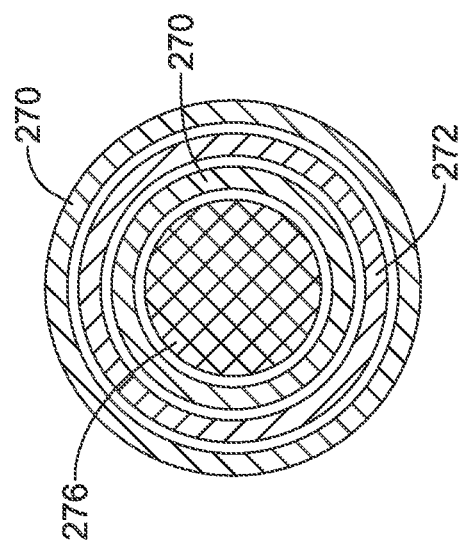
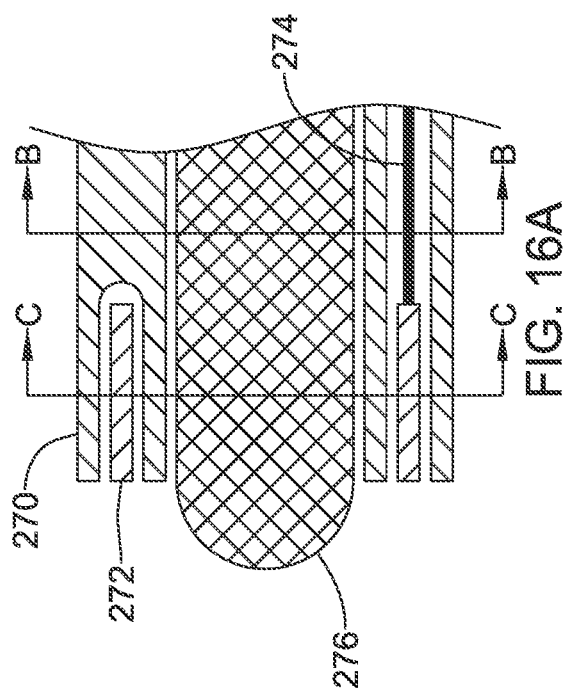
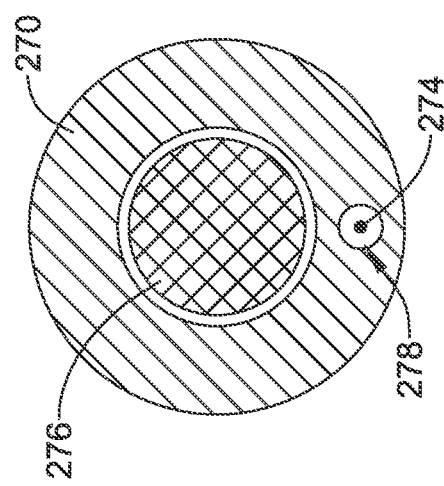

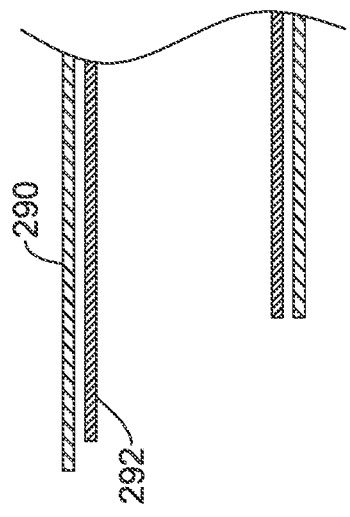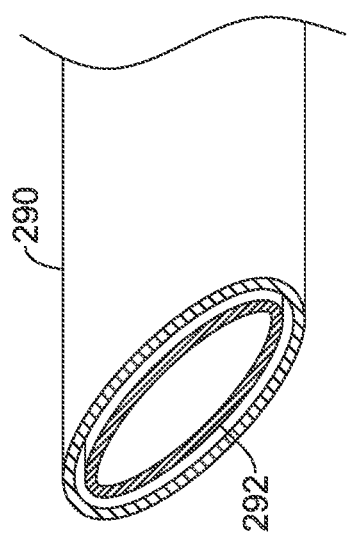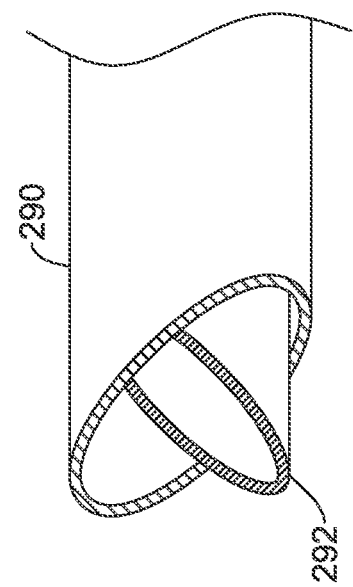

MINIMALLY INVASIVE METHOD TO IMPLANT A SUBCUTANEOUS ELECTRODE

CROSS REFERENCE TO RELATED APPLICATIONS

The present application claims the benefit of and priority to U.S. Provisional Application No. 62/195,700, filed Jul. 22, 2015, and titled MINIMALLY INVASIVE METHOD TO IMPLANT A SUBCUTANEOUS ELECTRODE, the disclosure of which is incorporated herein by reference.

BACKGROUND

The S-ICD System™ from Cameron Health, Inc., and Boston Scientific Corporation presents a new opportunity in cardiac rhythm management to reduce the complications associated with transvenous defibrillator systems. The defibrillator system itself may be implanted subcutaneously without accessing the vasculature or touching the heart.

An illustration is provided in FIG. 1. The system is implanted in a patient 10 with a canister 12 in the left axilla at about the level of the cardiac apex. A lead 14 is placed with a first portion extending subcutaneously along the inframammary crease to the xiphoid, and thence superiorly parallel to and 1-2 cm to the left of the sternum. A proximal sense electrode 16, shocking coil electrode 18, and distal tip sense electrode 20 are provided along the parasternal portion of the lead 14. The entire system is implanted outside of the ribcage. As shown in FIG. 2, a typical implant for the S-ICD System uses three incisions 30, 32, 34, and a sterile field represented by shape 36 shown is used to avoid the introduction of microorganisms that can cause infection. Some physicians have also used a two-incision technique foregoing the superior sternal incision 34.

The subcutaneous-only placement prevents some of the more dangerous complications associated with infection, in particular, endocarditis which can result when an infection travels down a transvenous lead into the heart. However, even with reasonable care, some patients will experience infection at the sternal incisions. In addition, some reports have shown that air pockets at either of incisions 32 or 34 can lead to inappropriate shocks within the first few weeks of implantation.

Alternatives to this implantation method are desired that would reduce the number of incisions.

OVERVIEW

The present inventors have recognized, among other things, that a problem to be solved is the inclusion of multiple incision locations in the implantation of a subcutaneous-only defibrillator. A minimally invasive technique and toolset is disclosed herein.

A first non-limiting example takes the form of an introducer tool kit for implantation of a subcutaneous lead for use in a cardiac therapy apparatus, the tool set comprising a first insertion tool for use in creating a first subcutaneous tunnel along a first line, having a distal end for introduction into a patient with an opening at or near the distal end, a first support member for placement through the first insertion tool during creation of the first subcutaneous tunnel, and a second insertion tool for use in creating a second subcutaneous tunnel at an angle relative to the first subcutaneous tunnel by passage through the first insertion tool and out of the opening, wherein the second insertion tool is configured to curve in a location at the opening of the first insertion tool.

A second non-limiting example takes the form of an introducer tool kit as in the first non-limiting example, further comprising a sheath for placement over the second insertion tool during passage through the first insertion tool and creation of the second subcutaneous tunnel. A third non-limiting example takes the form of an introducer tool kit as in the second non-limiting example, wherein the sheath is a splittable sheath adapted to remain in place during and after removal of the second insertion tool such that the subcutaneous lead may be introduced through the sheath into the second subcutaneous tunnel.

A fourth non-limiting example takes the form of a kit as in any of the first to third non-limiting examples, wherein the second insertion tool has a distal end which includes an actuatable element for establishing the second subcutaneous tunnel. A fifth non-limiting example takes the form of a kit as in any of the first to third non-limiting examples, wherein the second insertion tool has a distal end which includes an ultrasonic transducer for using ultrasonic energy to assist in creation of the second subcutaneous tunnel.

A sixth non-limiting example takes the form of an introducer tool set for implantation of a subcutaneous lead for use in a cardiac therapy apparatus, the tool set comprising an inner tunneling rod having a proximal end, a curvature at a first location, and a distal end adapted for dissecting a subcutaneous tunnel, the first location being nearer the distal end than the proximal end, an introducer sheath having a proximal end, a distal end, and an inner lumen sized to receive the inner tunneling rod in a slideable manner having at least a first relative configuration and a second relative configuration, wherein, when in the first relative configuration, the introducer sheath contains the curvature of the inner tunneling rod to maintain a generally straight assembly, and, when in the second relative configuration, the inner tunneling rod extends distal of the distal end of the introducer sheath at an angle to an axis of the introducer sheath.

A seventh non-limiting example takes the form of an introducer tool set as in the sixth non-limiting example, wherein the inner tunneling rod has a curvature of at least 60 degrees to facilitate creation of a subcutaneous tunnel having a first portion along a first line and a second portion along a second line that is at an angle of at least 60 degrees to the first line. An eighth non-limiting example takes the form of an introducer tool set of either of the sixth or seventh non-limiting examples, wherein the second configuration is such that the inner tunneling rod extends in the range of 2 to 6 inches beyond the distal end of the introducer sheath. A ninth non-limiting example takes the form of an introducer tool set as in any of the sixth to eighth non-limiting examples, wherein the introducer sheath is a powered sheath having an ultrasonic transducer.

A tenth non-limiting example takes the form of an introducer tool set as in any of the sixth to ninth non-limiting examples, wherein the inner tunneling rod includes a deployable cutting element to assist in dissecting through subcutaneous tissue. An eleventh non-limiting example takes the form of an introducer tool set as in any of the sixth to tenth non-limiting examples, wherein the inner tunneling rod is a powered tool having an ultrasonic transducer.

A twelfth non-limiting example takes the form of an introducer tool set as in any of the sixth to eleventh non-limiting examples, further comprising a guidewire for passage through at least one of the inner tunneling rod or the sheath, configured to be left in the subcutaneous tunnel during removal of the sheath and the inner tunneling rod, and a dilator for passage over the guidewire to expand a subcutaneous tunnel made with the sheath and the inner tunneling rod. A thirteenth non-limiting example takes the form of an introducer tool set as in the twelfth non-limiting example, further comprising a splittable sheath configure for placement on the dilator during passage over the guidewire, the splittable sheath configured to remain in place during removal of the guidewire and dilator to facilitate introduction of the subcutaneous lead therethrough, wherein the splittable sheath is configured such that once the subcutaneous lead is placed, the splittable sheath can be split and removed thereover.

A fourteenth non-limiting example takes the form of an introducer tool set as in any of the sixth to thirteenth non-limiting examples, wherein the inner tunneling rod is a steerable rod having a steering mechanism to selectively impart the curvature. A fifteenth non-limiting example takes the form of an introducer tool set as in any of the sixth to thirteenth non-limiting examples, wherein at least one of the inner tunneling rod or the introducer sheath comprises a force sensor configured to identify forces applied during insertion thereof.

A sixteenth non-limiting example takes the form of a method of implanting a subcutaneous defibrillation lead in a patient comprising making a first incision, inserting a first insertion tool having a distal end and a proximal end via the first incision and directing the first insertion tool to a target location to establish a first subcutaneous tunnel from the incision toward the target location, and extending a second insertion tool from within the first insertion tool, wherein the first insertion tool extends generally along a first axis and the second insertion tool is extended from at or near the distal end of the first insertion tool along a second axis at an angle of at least 30 degrees from the first axis, to form at least a portion of a second subcutaneous tunnel along the second axis.

A seventeenth non-limiting example takes the form of a method as in the sixteenth non-limiting example, wherein the first insertion tool is a powered tool having an ultrasonic transducer to facilitate tunneling through tissue, and the step of inserting the first insertion tool comprises activating the ultrasonic transducer. An eighteenth non-limiting example takes the form of a method as in either of the sixteenth or seventeenth non-limiting examples, wherein the first insertion tool comprises a lumen having an exit at or near the distal end of the first insertion tool, and the second insertion tool is a blunt dissector having a curve near its distal end to facilitate creating the angle of at least 30 degrees, such that the step of extending the second insertion tool from within the first insertion tool comprises generating the angle using the curve of the second insertion tool.

A nineteenth non-limiting example takes the form of a method as in the sixteenth non-limiting example, wherein the second insertion tool is steerable and includes a steering control at the proximal end thereof, and the step of extending the second insertion tool includes steering the distal end thereof in a desired direction toward the second axis. A twentieth non-limiting example takes the form of a method as in the sixteenth non-limiting example, wherein the second insertion tool includes a deployable cutter for facilitating advancement of the second insertion tool, and the step of extending the second insertion tool comprises using the deployable cutter to direct the second insertion tool along the second axis.

A twenty-first non-limiting example takes the form of a method as in any of the sixteenth to twentieth non-limiting examples, wherein the second axis is at an angle of about 90 degrees from the first axis. A twenty-second non-limiting example takes the form of a method as in any of the sixteenth to twenty-first non-limiting examples, wherein the first axis generally extends along a transverse plane of the patient, and the second axis generally extends along a sagittal or parasagittal plane of the patient. A twenty-third non-limiting example takes the form of a method as in any of the sixteenth to twenty-second non-limiting examples, wherein the first subcutaneous tunnel extends from approximately the left axilla toward the sternum, and the second subcutaneous tunnel extends from a location 1-5 cm left and superior to the xiphoid toward the manubrium in a direction generally parallel to the sternum.

A twenty-fourth non-limiting example takes the form of a method as in the sixteenth non-limiting example, wherein the second insertion tool comprises a proximal end with a handle and a distal end, and the step of extending the second insertion tool includes using a blunt dissector placed within the second insertion tool to dissect tissue, wherein the second insertion tool is used to determine the direction in which the blunt dissector is directed, and the blunt dissector is configured for longitudinal strength but not lateral strength. A twenty-fifth non-limiting example takes the form of a method as in the twenty-fourth non-limiting example, wherein the second insertion tool is steerable and includes a steering control at the proximal end thereof, and the step of extending the second insertion includes steering the distal end thereof in a desired direction toward the second axis with the blunt dissector therein.

A twenty-sixth non-limiting example takes the form of a method as in the twenty-fourth non-limiting example, further comprising advancing the blunt dissector from the distal end of the second insertion to form the second subcutaneous tunnel such that the first insertion tool extends from the first incision to the target location, the second insertion tool extends from the distal end of the first insertion tool along a curve to the start of the second subcutaneous tunnel, and the blunt dissector extends from the start of the second subcutaneous tunnel to a distal end thereof.

A twenty-seventh non-limiting example takes the form of a method as in the twenty-sixth non-limiting example, wherein the blunt dissector is provided with a lumen therein for advancement or placement of a guidewire, and the method further comprises advancing the guidewire through the lumen to near or at the distal end of the second subcutaneous tunnel, removing at least the blunt dissector while keeping the guidewire in a desired place, advancing a lead over the guidewire to a desired lead position, and removing the guidewire.

A twenty-eighth non-limiting example takes the form of a method as in the twenty-sixth non-limiting example, wherein the blunt dissector is provided with a lumen for advancement or placement of a guidewire, and the step of advancing the blunt dissector is performed with the guidewire contained in the lumen of the dissector and the method further comprises removing at least the blunt dissector over the guidewire while keeping the guidewire in a desired place, advancing a lead over the guidewire to a desired lead position, and removing the guidewire.

A twenty-ninth non-limiting example takes the form of a method as in the twenty-sixth non-limiting example, wherein step of advancing the blunt dissector is performed with a tearable sheath thereover, and the method further comprises removing at least the blunt dissector while keeping the sheath in a desired place, advancing a lead within the tearable sheath to a desired lead position, and removing the tearable sheath over the lead.

A thirtieth non-limiting example takes the form of a method as in the sixteenth non-limiting example, wherein the second insertion comprises a dissection tool therein having a tip for direction advancement into tissue, wherein the step of extending the second insertion includes using the dissection tool tip to selectively dissect tissue in the direction of the second axis. A thirty-first non-limiting example takes the form of a method as in the sixteenth non-limiting example, further comprising advancing the second insertion tool such that a distal tip thereof is at or near a desired position, advancing the first insertion tool over the second insertion tool such that the distal end of the first insertion tool is at or near the desired position, removing the second insertion tool from within the first insertion tool, inserting a lead having a proximal end and a distal end such that the distal end thereof is at or near the desired position, and removing the first insertion tool over the lead. A thirty-second non-limiting example takes the form of a method as in the thirty-first non-limiting example, further comprising anchoring the lead such that its distal end will remain at or near the desired position. A thirty-third non-limiting example takes the form of a method as in any of the sixteenth to thirty-second non-limiting examples, further comprising closing the first incision such that the method is completed without making a second incision. A thirty-fourth non-limiting example takes the form of a method as in any of the sixteenth to thirty-second non-limiting examples, further comprising closing the first incision such that the method is completed using only a single incision.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 16A-16D and 17A-17C show illustrative cutting mechanisms; and

DETAILED DESCRIPTION

Figure 1:
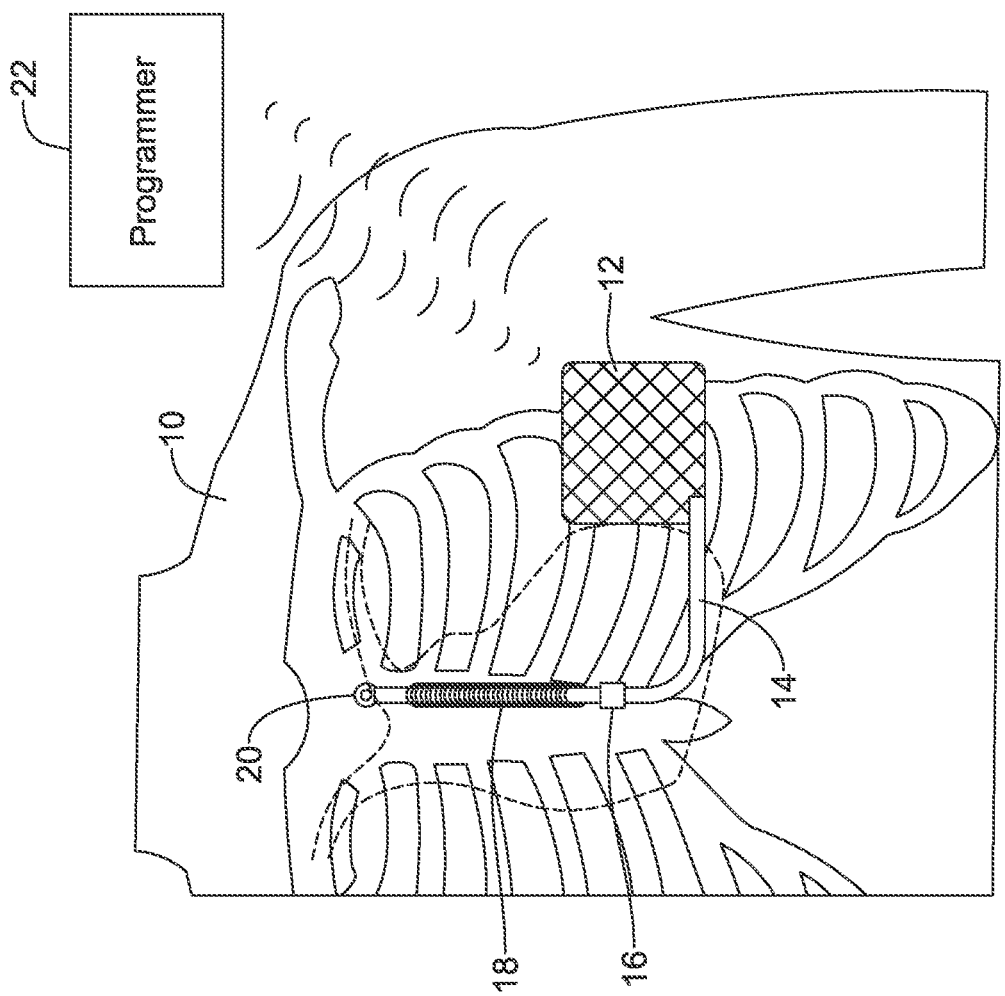
FIG. 1 shows an illustrative subcutaneous-only implantable cardiac stimulus system in an implanted state.
Figure 2:
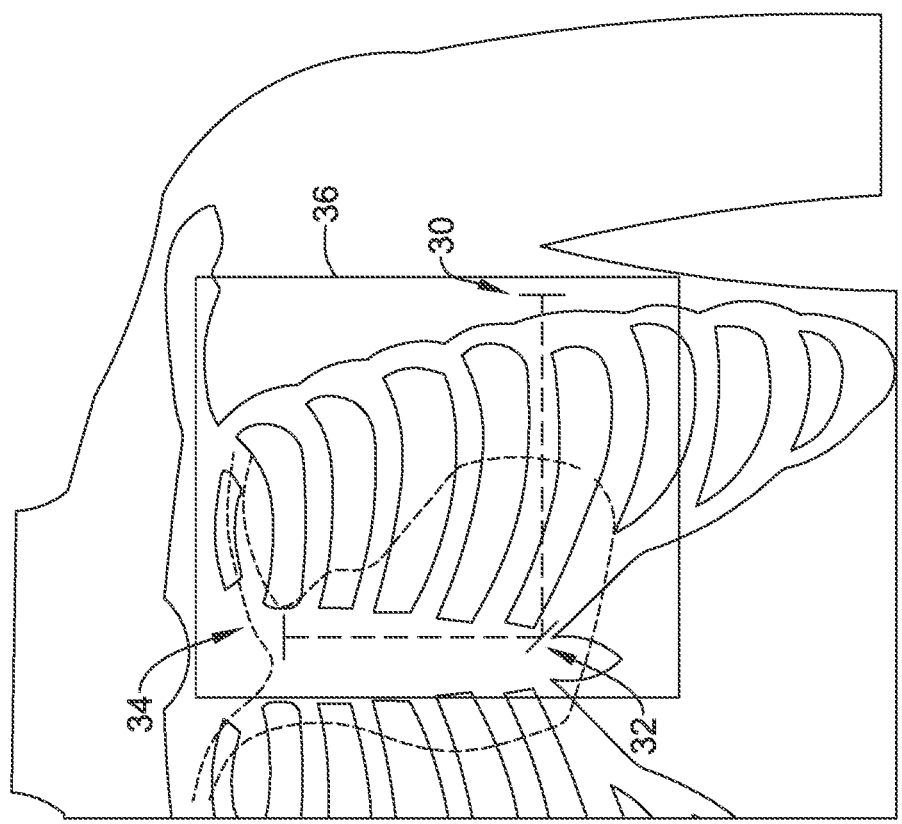
FIG. 2 illustrates certain aspects of the procedure to implant a device as in FIG. 1.

As explained above, FIG. 1 shows an illustrative subcutaneous-only implantable cardiac stimulus system in an implanted state. FIG. 2 illustrates certain aspects of the procedure to implant a device as in FIG. 1. In this illustration, the procedure for implantation calls for the use of three incisions at locations 30, 32 and 34. To reduce the risk of infection, a sterile field including approximately area 36 may be prepared. This largely tracks the method of implant described in the labeling approved in the United States for the S-ICD® System from Cameron Health and Boston Scientific at the time of commercial approval in 2012.

However, in many patients, this sterile field 36 will include various skin folds, for example with obese patients and/or due to proximity to the left breast. It is not always easy to get this area 36 clean for surgery, let alone keeping it clean and dry during the days or weeks after surgery while the incisions 30, 32, 34 all heal. For some patients, the incisions along the sternum may also present aesthetic concerns, for example, because incision 34 may leave a scar that can be visible when wearing ordinary and common clothing and incision 32 may be clearly visible when wearing swimwear.

Reducing the number of incisions has been proposed. Some may use, for example, a two-incision technique similar to that described in some embodiments of U.S. Pat. No. 7,655,014, the disclosure of which is incorporated herein by reference. In this technique, after tunneling between incision 32 and incision 30 and pulling the lead therethrough, an introducer tool having a splittable sheath is advanced from incision 32 toward the manubrium along the sternum, without making incision 34 at all. Next, the introducer tool is removed, leaving the sheath behind, and the lead is introduced through the sheath. Finally the sheath is split and removed over the lead.

One refinement is suggested in U.S. Pat. No. 6,647,292, in which the implantable defibrillator has a unitary structure. An elongated housing is provided with electrodes on each end and inserted through a single incision in the patient. A dissection tool may be used to create a space for the implant to take place. However, this system requires an elongated, curved housing containing all the required electronics of the device. While curved housings can be developed, it is believed to be cheaper and simpler to provide a compact housing having a rectangular, oval or round shape, rather than the elongated curves of U.S. Pat. No. 6,647,292. Therefore the present inventors have identified ways to implant a lead along a subcutaneous path having a curve in the middle of the path as further described below.

Figure 3:
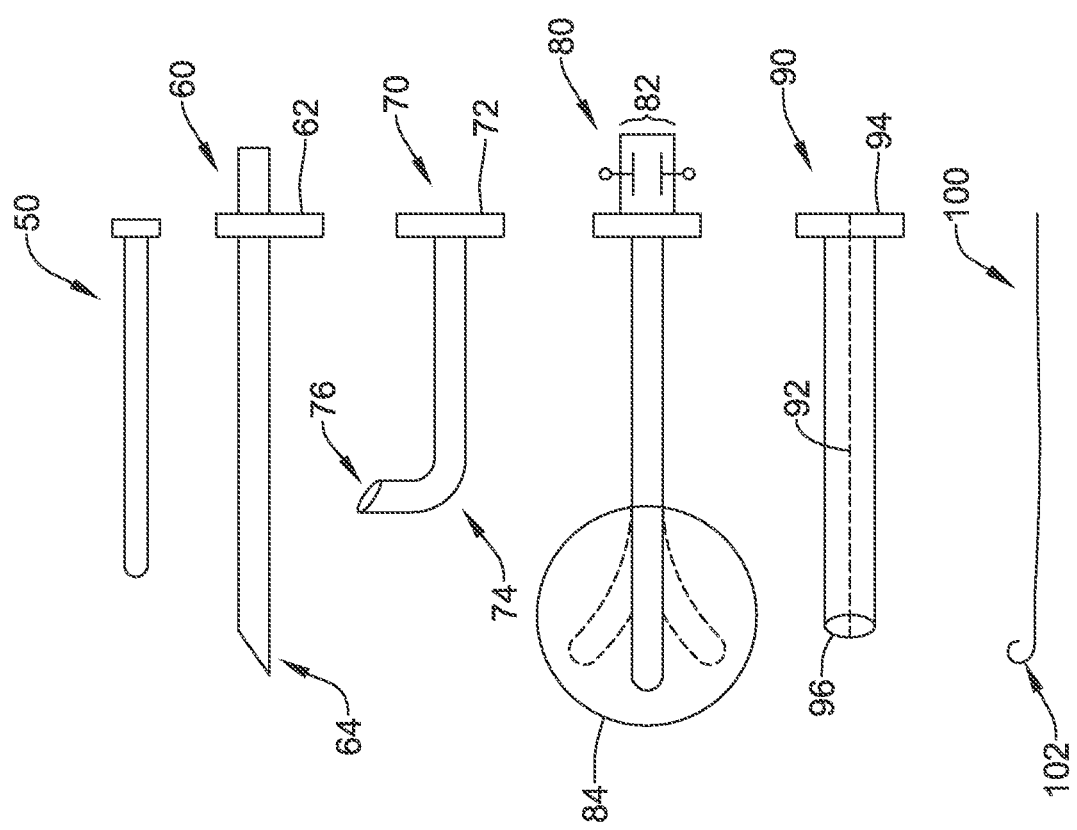
FIG. 3 shows an introducer tool set or kit for an illustrative example.

FIG. 3 shows an introducer tool set or kit for an illustrative example. A set of tools may include a blunt dissector 50, a first insertion tool 60, a second insertion tool 70, a steerable insertion tool 80, a splittable sheath 90, and a guidewire 100. Not all elements may be provided in a single kit. For example a kit may include the blunt dissector 50, the second insertion tool 70, and the guidewire 100, without the other elements. Another illustrative kit includes the first insertion tool 60, the steerable insertion tool 80, and the splittable sheath 90. As with other figures herein, FIG. 3 is not necessarily drawn to scale; different items may be longer or shorter than others, and relative thickness to length ratios are not to scale.

The blunt dissector 50 has a proximal end with a handle and a distal tip adapted for bluntly dissecting subcutaneous tissue. In various examples, the blunt dissector 50 may be solid or hollow, or may have a lumen with a distal opening. The blunt dissector 50 may be made of any suitable biocompatible material including polymers, metals, or combinations thereof such as a polymeric shaft with a braided or coiled metal support member, for example. The distal tip of the blunt dissector may be blunted or, in some embodiments, may be pointed or sharp to facilitate advancement through subcutaneous tissue. In one example, the blunt dissector 50 may include two or more pieces such as an elongated hollow element and a dilator for insertion therethrough.

The first insertion tool 60 is an elongate member having a lumen therethrough extending from the handle 62 to a distal tip 64. The elongated member is preferably a polymeric tube which may include a braided or other support member therein. The distal tip 64 is shown has having an angled or beveled shape. The first insertion tool 60 may include, in some embodiments, an actuator and cutting element near the distal tip 64. If desired, the proximal handle 62 may include a port to facilitate fluid infusion therethrough, for example, to allow an antibiotic or analgesic to be introduced.

In some examples, the distal tip 64 may include an ultrasound transducer coupled to a conductor that is accessible at the proximal handle 62 of the first insertion tool 60. Such a transducer may be useful to assist in tissue dissection during passage through subcutaneous tissue. The handle 62 may be lopsided as shown, or may otherwise be marked, to help the user identify which direction the angled end of the distal tip 64 is facing at a given time.

The first insertion tool 60 is shown as a generally straight element. A second insertion tool 70 is shown as well, with a handle at 72 and an elongated shaft extending to a curve at 74 and distal tip 76. The curve 74 can be provided at a desired distance from the handle 72 to accommodate, for example, the spacing between a patients left axilla and xiphoid since, in some example, the intention is to implant a device such as that shown in FIG. 1 using only a single incision location at the left axilla. The curve may be a result of a specific support structure (such as a braided or woven element), heat-curing, shape memory, or manufacturing using a mold, for example.

The second insertion tool 70 is sized so its diameter fits within the elongated shaft of the first insertion tool 60. In some examples, the first insertion tool 60 includes a shaft which is resistant to lateral pressure such that the second insertion tool 70, when placed inside the first insertion tool 60, is held in a generally straight orientation without curve 74. For example the first insertion tool may be formed of or include a section formed of a hypotube resistant to bending overall or just in a select region thereof. For such examples, the length of the second insertion tool 70 may be such that it can be advanced so that the distal tip 76 and curve 74 exit the distal end 64 of the first insertion tool 60.

A steerable insertion tool is shown at 80 and may, in some examples, take the place of the second insertion tool 70. The proximal handle 82 of the steerable insertion tool 80 may include one or more actuators for steering the distal end 84 thereof. The distal end 84 can be configured as a dissection tip, or there may be a lumen through the steerable insertion tool 80 that opens at the distal end 84. Steerability may be imparted, by any suitable design such as those well known in endoscopy. For example, a steering wire or wires may be provided such that pulling on the steering wire at the proximal handle 82 deflects the distal end 84.

A splittable sheath 90 is shown as well, with a splittable handle 94 and a line of weakness or perforation 92 extending to a distal end 96 thereof. Such sheaths are well known in the art. Finally, a guidewire 100 is shown, which may take any suitable form including various known and commercially available guidewires in any suitable size.

In some examples, the distal ends of any of items 50, 60, 70, or 80 may include one or more light emitting elements such as light emitting diodes to assist the physician in transcutaneously visualizing the position of the distal end during implantation. Any of items 50, 60, 70, 80, or 100 may include, for example, a Doppler detector or other sensor to assist the physician in knowing when a tissue transition has been reached to prevent, for example, piercing through undesired tissue such as an intercostal space or pectoral muscle. Such markers or detectors may also assist in determining whether the advancing insertion tool is close to or penetrating muscle such as the pectoral muscle, indicating the insertion path may be too far lateral from the sternum (assuming without limitation that the desired path would be near the sternum).

Figure 4:
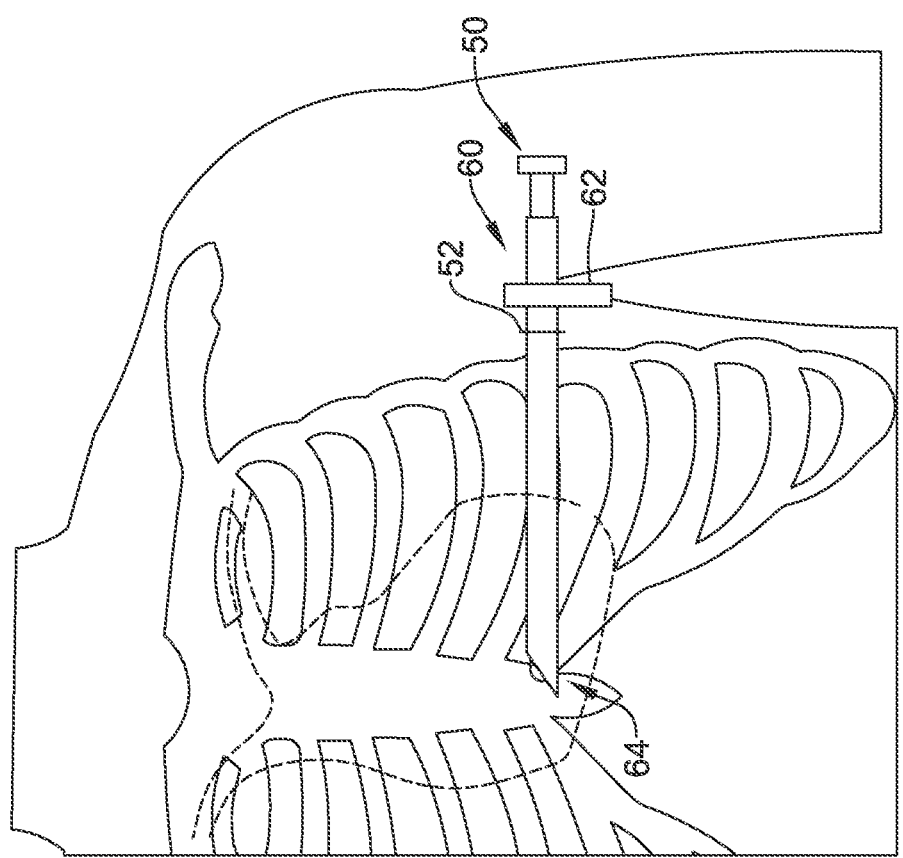
FIGS. 4-5 and 7-8 illustrate the use of a tool set as in FIG. 3 to implant a medical device.

FIGS. 4-5 and 7-8 illustrate the use of a tool set as in FIG. 3 to implant a medical device. In FIG. 4, a blunt dissector 50 is placed through a first insertion tool 60 such that it extends just beyond the distal tip of the first insertion tool 60. The combination of blunt dissector 50 and first insertion tool 60 has been inserted through an incision 52 at approximately the anterior axillary line of the patient. Prior to making incision 52 a physician's team will have first created a proper sterile field around at least the incision 52.

The inserted elements 50/60 have been directed toward the patient's axilla, with the distal tip of the blunt dissector 50 used to dissect a subcutaneous tunnel. If desired, rather than simply the blunt dissector 50, a steerable element may be used during the step shown in FIG. 4. In another alternative, the steerable element 80 and second insertion tool 70 (FIG. 3) may be used during the first insertion step shown in FIG. 4, rather than the blunt dissector 50.

Figure 5:
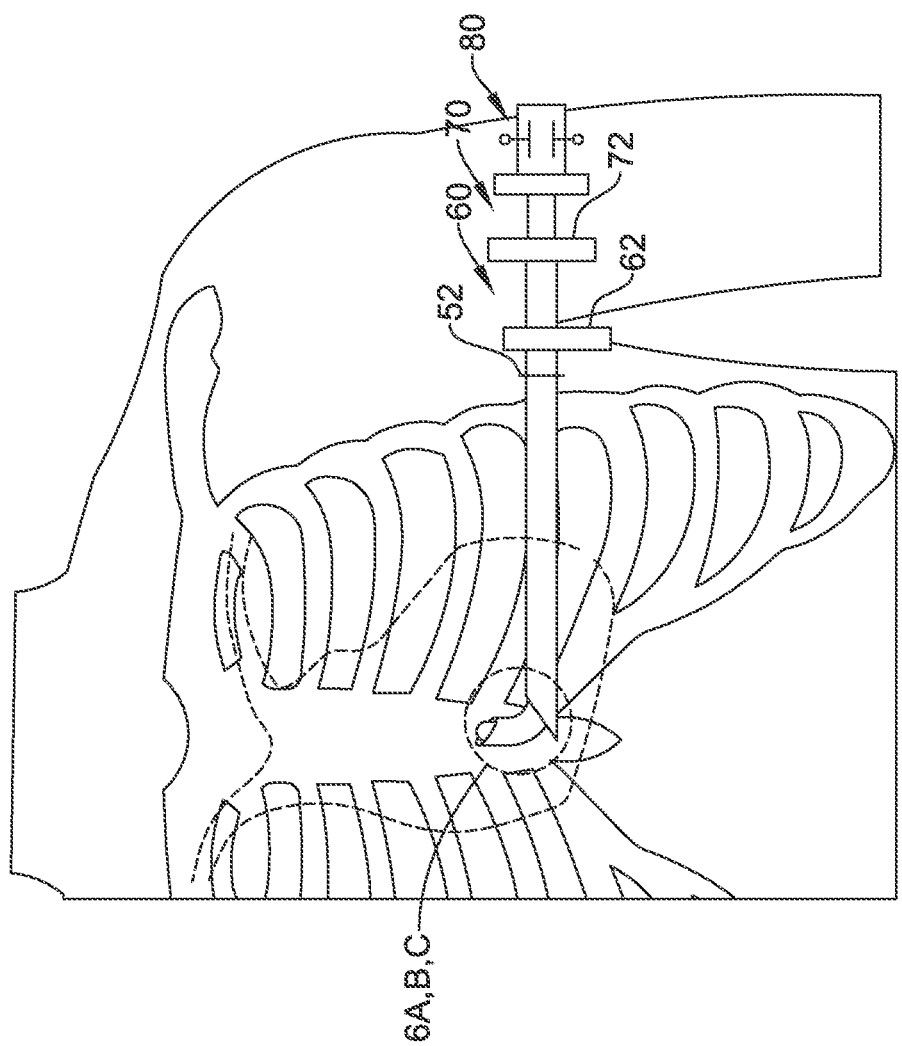

FIG. 5 shows a next step, in which a second insertion tool 70 has been inserted into the first insertion tool 60, with a curve at the end of the second insertion tool 70 used to extend past the distal tip of the first insertion tool 60. In this example, a steerable insertion tool 80 has been used as a dilator within the second insertion tool 70 to facilitate introduction and turning as highlighted in FIGS. 6A-6C. If a blunt dissector 50 was used in the preceding step, as shown in FIG. 4, that tool would have been first removed to allow introduction of items 70/80.

Figure 6B:
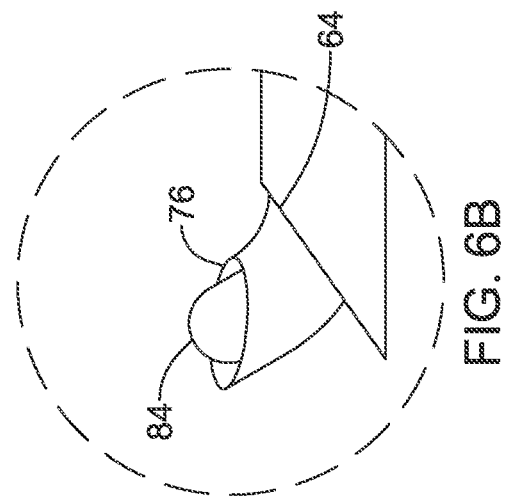
FIGS. 6A-6C provide detail views of steps illustrated in FIG. 5.
Figure 6C:
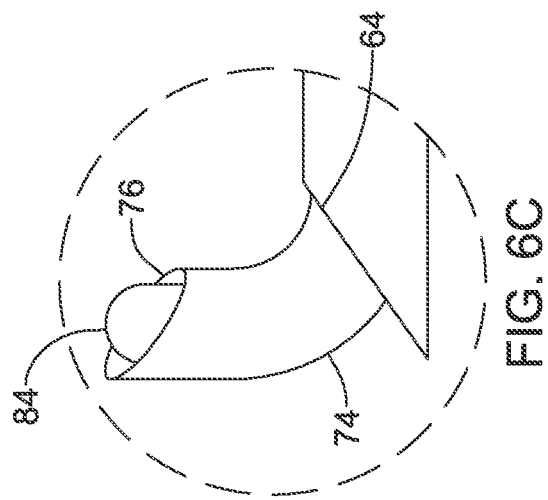
Figure 6A:
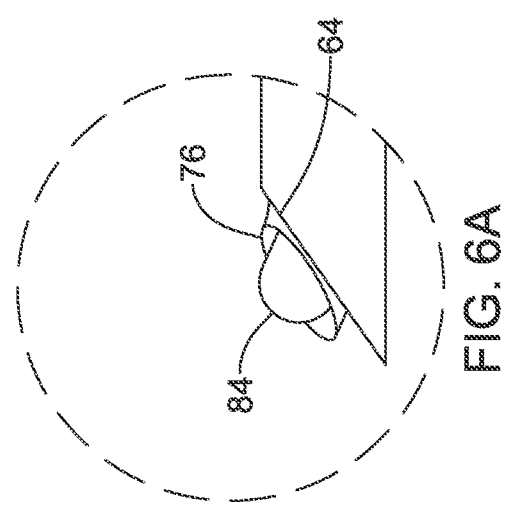

FIGS. 6A-6C provide detail views of steps illustrated in FIG. 5. As shown in FIG. 6A, the distal tip 76 of the second insertion tool extends just beyond the distal tip 64 of the first insertion tool. In addition, the distal tip 84 of the steerable insertion tool extends out from the distal tip 76 of the second insertion tool.

FIG. 6B shows that the steerable insertion tool has been deflected at its distal end 84 to guide the distal end 76 of the second insertion tool along a direction that is at an angle with the axis of the first insertion tool. The steerable insertion tool and the second insertion tool may be advanced together during this process, or distal tip 84 of the steerable insertion tool may be advanced first such that the second insertion tool would next be advanced over the steerable insertion tool. The first or second insertion tools, or the steerable insertion tool, may also include a sharp cutting element (not shown) to facilitate advancement, if desired, using small, short cutting movements to provide a controlled advance through a desired angle.

FIG. 6C shows that the distal tips 76, 84 of the second insertion tool and steerable insertion tool advance further, allowing a precurved portion 74 of the second insertion tool to exit the distal end 64 of the first insertion tool. In an example, the precurved portion 74 of the second insertion tool can be less stiff than the first insertion tool, or a portion thereof, and/or the combined stiffness of the first insertion tool and the steerable insertion tool, to keep the precurved portion 74 straight until it exits the distal end 64 of the first insertion tool. In another example, one or both of the steerable insertion tool or second insertion tool may include an open lumen for receiving a stiff wire or stylet which may be removed to release the precurved portion 74 when desired.

Figure 7:
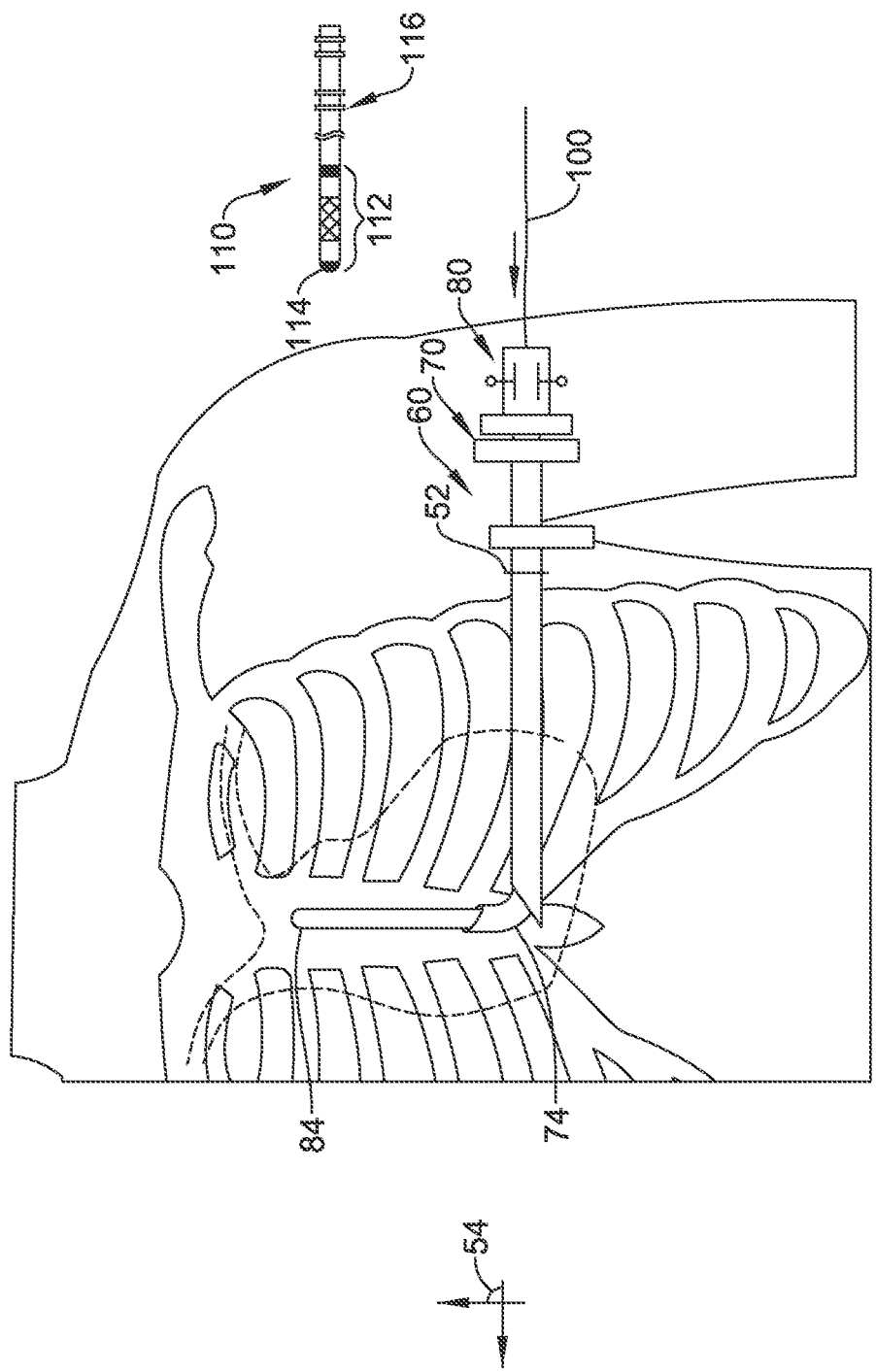

As shown in FIG. 7, once the precurved portion 74 of the second insertion tool exits the distal end of the first insertion tool, it can serve as the base for advancing the steerable insertion tool 80 in the parasternal direction until the distal tip thereof is somewhere in the range of the $2^{nd}$ to $4^{th}$ ribs, just inferior to the manubrium (other locations may be chosen). As shown in FIG. 7, an angle 54 is defined by a first axis along a line from the axillary incision to the end of the first insertion tool, and a second axis that runs generally parallel to the sternum, as the steerable insertion tool 80 is extended. The angle 54 may be in the range of 30 to 135 degrees; in the example shown, the angle 54 would be about 90 degrees or may be in the range of 75 to 105 degrees.

A lead 110 is also shown, and includes an electrode configuration 112 near a distal tip 114, and a proximal end 116 which may have a seal plug and a plurality of electrical contacts. Any suitable lead 110 may be used; some illustrative examples are shown in U.S. Pat. No. 8,483,841, though other designs may be used as well.

Figure 8:
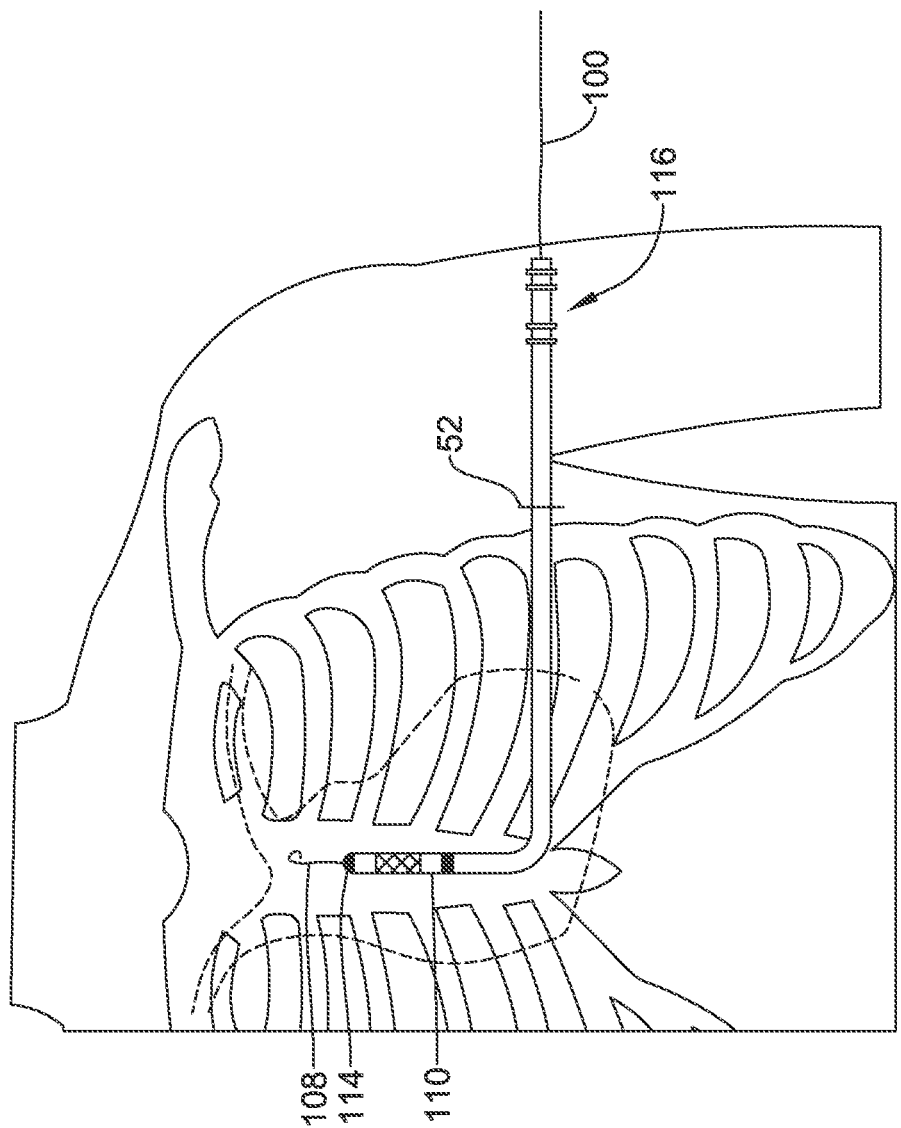

In some embodiments the next step would be to remove the steerable insertion tool 80 and simply introduce the lead 110 through the first and second insertion tools 60, 70 and up the subcutaneous tunnel formed by the advancement of the steerable insertion tool 80. In the example shown in FIG. 7, however, a guidewire is introduced through the steerable insertion tool 80 until it exits at or near the distal tip thereof. The steerable insertion tool 80 is then removed and, as shown in FIG. 8, the lead 110 is advanced over the guidewire 100. If desired, the steerable insertion tool 80 may include a side port or side channel to act as a rapid-exchange or single-operator exchange mechanism, in the manner known in the catheter arts, to avoid having to handle the entire length of the steerable insertion tool 80 over the guidewire 100 outside of the patient.

As an alternative to use of the guidewire 100 in FIG. 8, a splittable sheath (such as element 90 in FIG. 3) may be placed over the steerable insertion tool 80 before it is inserted. Once the parasternal subcutaneous tunnel is formed, the steerable insertion tool 80 would be removed, while keeping the splittable sheath in place, and the lead 110 would be inserted through the splittable sheath.

In another embodiment, the process shown to achieve the result in FIG. 8 may be performed with relatively small diameter devices, too small to achieve a tunnel large enough to implant a subcutaneous lead. Smaller devices may allow for easier tunneling with high precision, for example. For this example, once the guidewire 100 is in place, the remaining devices can be removed leaving only the guidewire, and a dilator is then introduced over the guidewire to expand the subcutaneous tunnel for introduction of the lead. If desired, the guidewire 100 may include an anchoring element, such as an inflatable balloon, at or near its distal tip, so that the guidewire can be anchored in place during removal of the other devices and advancement of the dilator.

Figure 9:
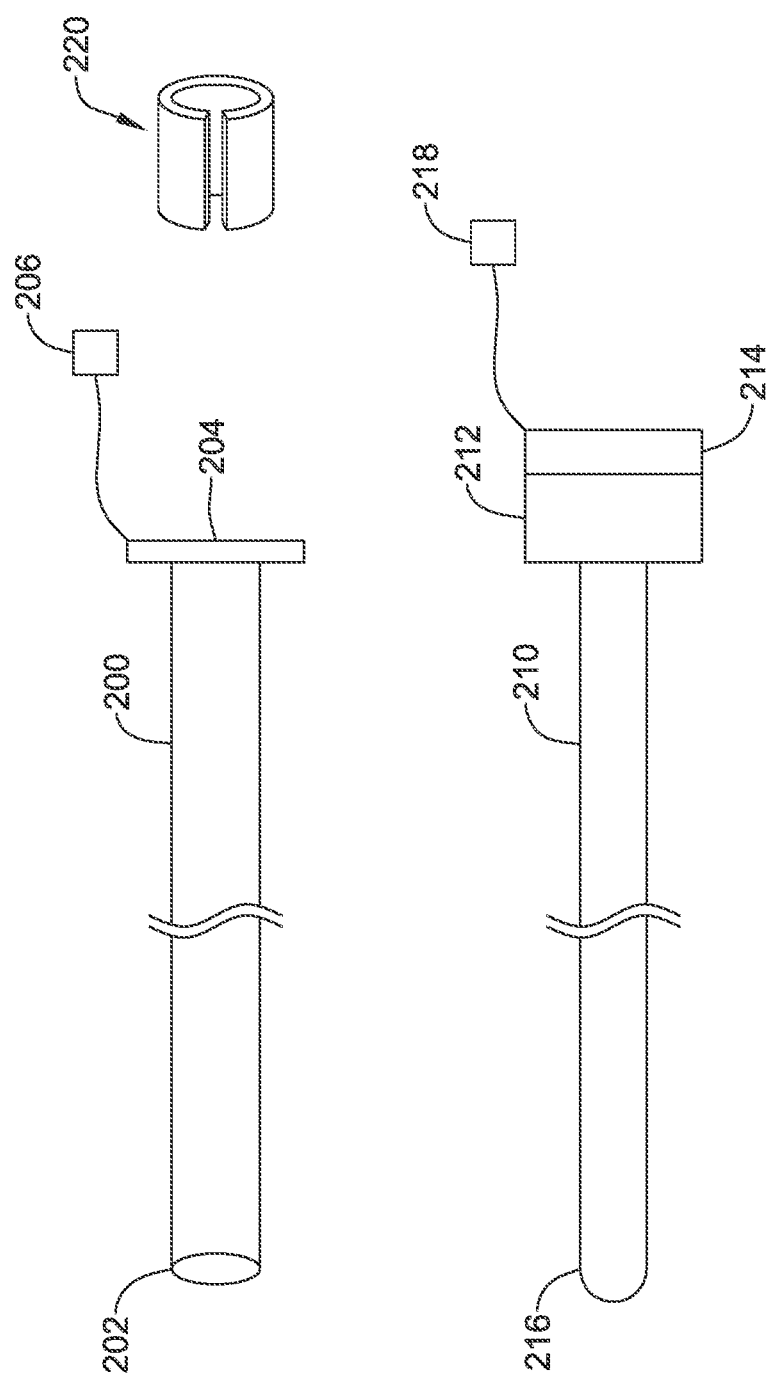
FIG. 9 shows an introducer tool set or kit for another illustrative example.

FIG. 9 shows an introducer tool set or kit for another illustrative example. A first insertion tool 200 includes a distal end 202 and a proximal port 204, with a lumen (not shown) extending between the proximal port 204 and the distal end 202. Optionally the first insertion tool 200 may be a powered insertion tool having a driver 206 for an ultrasonic transducer near the distal end 202 to facilitate advancement through subcutaneous tissue.

A second insertion tool is also shown at 210, having a two-part proximal handle 212, 214 and a distal tip 216. The distal tip 216 may be a cone or bullet shaped tip to facilitate subcutaneous dissection. Again, optionally, the second insertion tool may be a powered insertion tool having a driver 218 for an ultrasonic transducer near the distal tip 216 to facilitate advancement through tissue. In an example the distal tip 216 is designed with a cutting element that can be actuated by twisting one part of the handle 212 relative to the other part of the handle 214, as illustrated below in FIGS. 17A-17C. Alternatively, the two part handle 212, 214 may facilitate control over a steering mechanism at the distal tip 216.

Also optional is a spacing tool 220 that can be used as shown below to maintain a desired longitudinal relationship between the first insertion tool 200 and the second insertion tool 210 during certain steps of a method of implantation. The spacing tool 220 may have any suitable configuration and is shown in this example as a C-shaped element designed to snap fit over the second insertion tool distal of the handle 212, 214.

Figure 10:
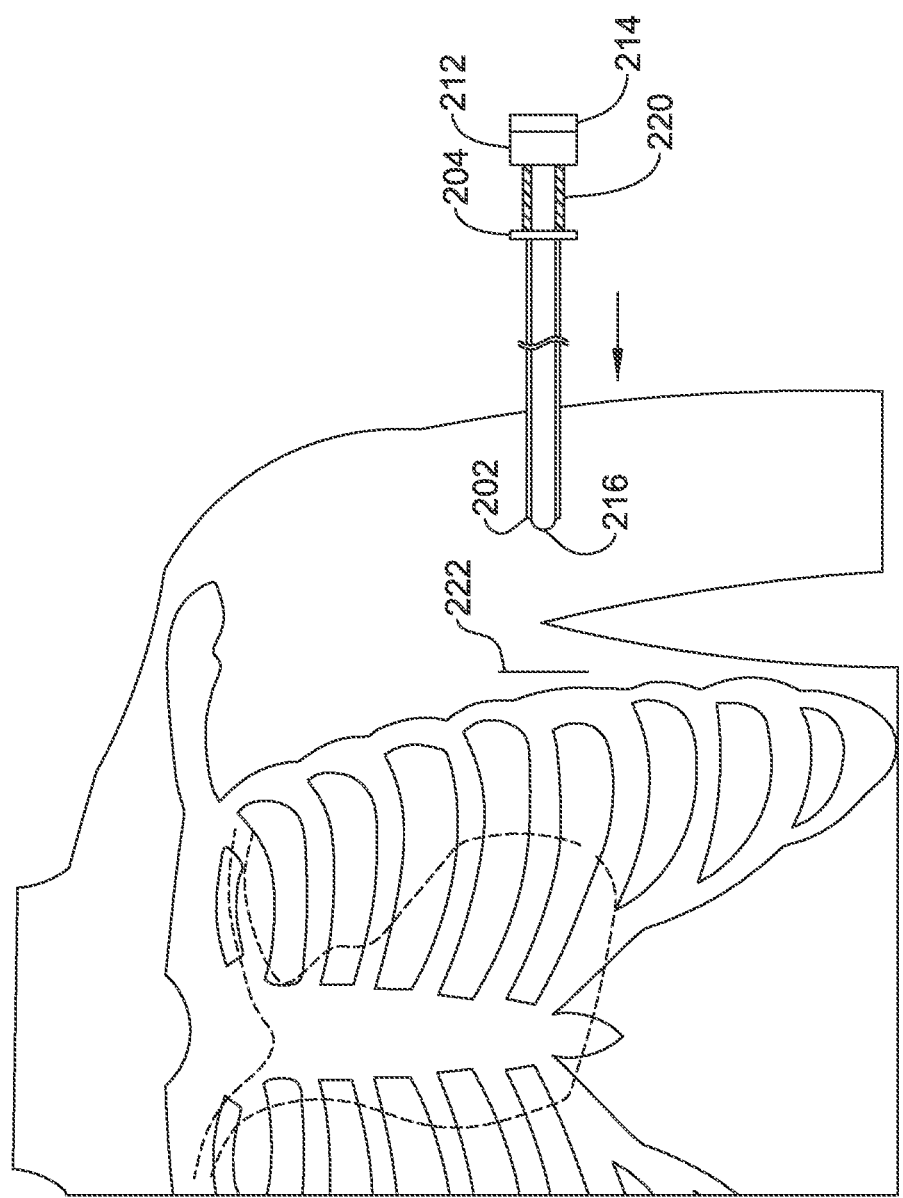
FIGS. 10-12 and 14 illustrate the use of a tool set as in FIG. 9 to implant a medical device.

FIGS. 10-12 and 14 illustrate the use of a tool set as in FIG. 9 to implant a medical device. FIG. 10 illustrates a pre-insertion step in which an incision 222 has been made on the patient following normal sterile field preparation. The insertion tools of FIG. 9 have been coupled together as shown, with the handle 204 of the first insertion tool spaced from the handle 212 of the second insertion tool by the spacer 220. The use of the spacer maintains the distal tip 216 of the second insertion tool in a desired configuration extending just beyond the distal tip 202 of the first insertion tool during insertion.

Figure 11:
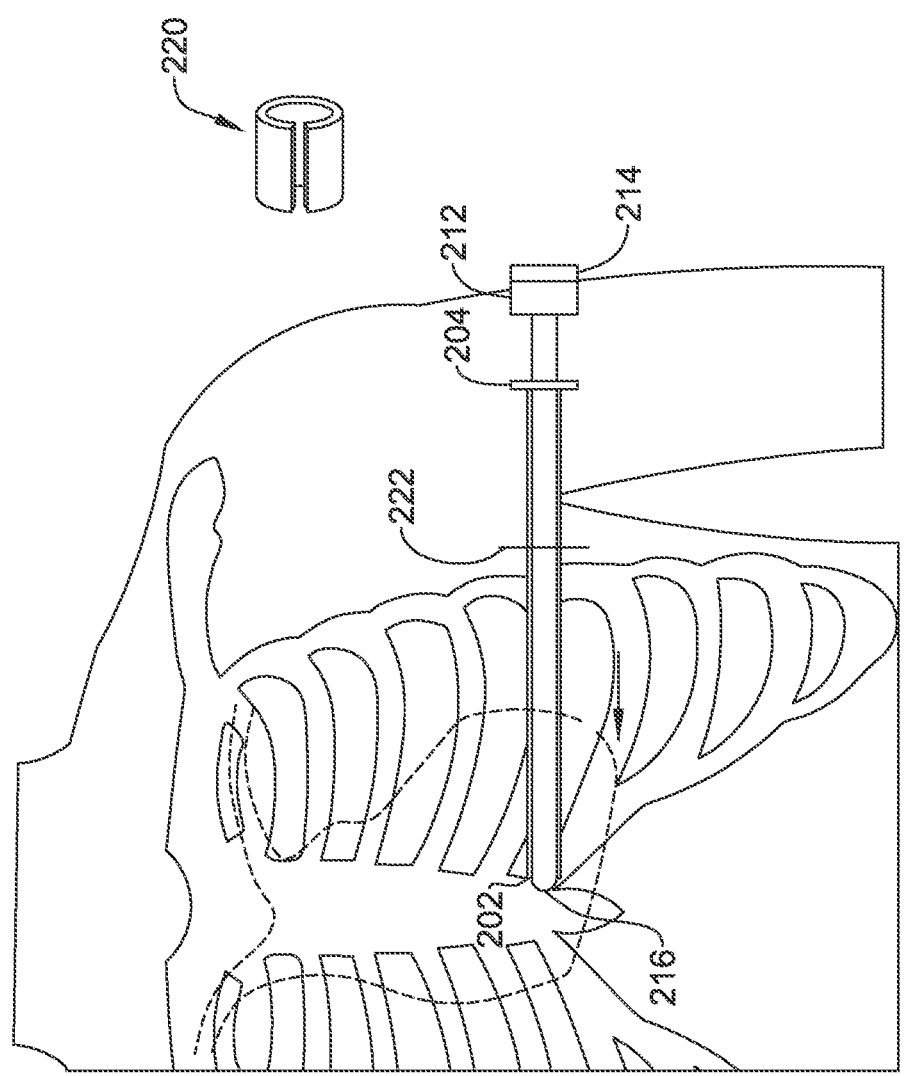

FIG. 11 shows a next step, with the insertion tools together tunneled through the incision toward the xiphoid of the patient, using the distal tip 216 of the second insertion tool to dissect through the subcutaneous tissue. Upon reaching the xiphoid, the spacer 220 can be removed, as shown. Next, as shown in FIG. 12, the two part handle 212, 214 can be manipulated to advance the distal end 216 of the second insertion tool to turn superiorly as detailed in FIGS. 13A-13D.

Figure 12:
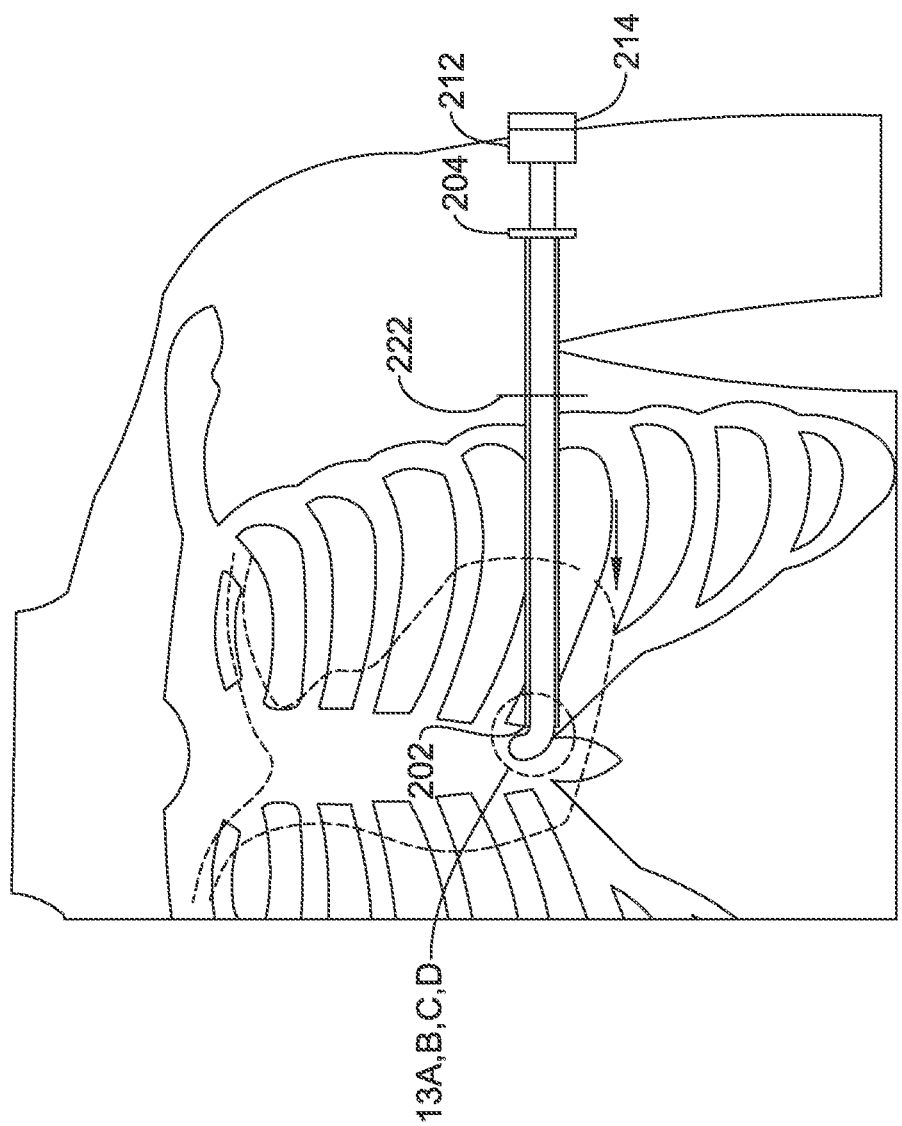
Figure 13A:
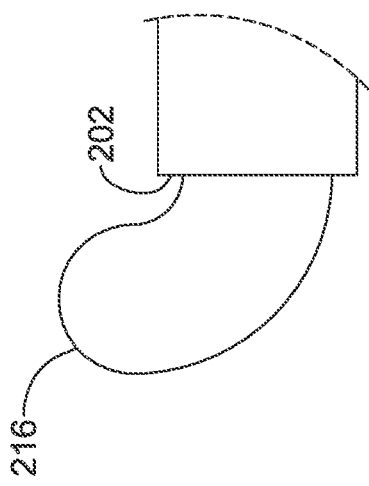
FIGS. 13A-13D provide detail views of steps illustrated in FIG. 12.
Figure 13B:
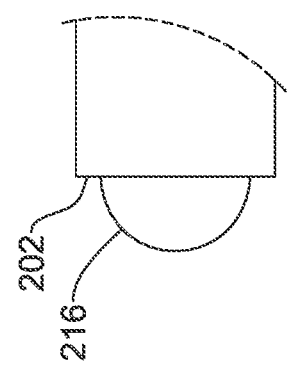

FIGS. 13A-13D provide detail views of steps illustrated in FIG. 12. As shown at FIG. 13A, the spacer, when used, keeps the distal end of the second insertion tool 216 just distal of the distal tip 202 of the first insertion tool. With the spacer removed, the second insertion tool is inserted further into the first insertion tool, allowing the tip 216 to extend farther away from tip 202, as shown at FIG. 13B.

There are several design options available to create the turn shown in FIG. 13B. In one example, a steering mechanism can be used, either by manipulating the two part handle, or some other feature such as a pull string or lever, to steer the distal tip 216. In another example, the second insertion tool is precurved and kept straight by the first insertion tool shaft during insertion, and once the distal tip 216 is advanced, the natural curve of the second insertion tool is allowed to create the shape shown. In a variant on the pre-curved design, the first insertion tool may include one or more removable stiffeners to maintain the straight configuration. In yet another example, a cutting element is provided at the distal end 216 as shown below in FIG. 16A-16D or 17A-17C and is used to selectively cut tissue toward the desired direction.

Figure 13C:
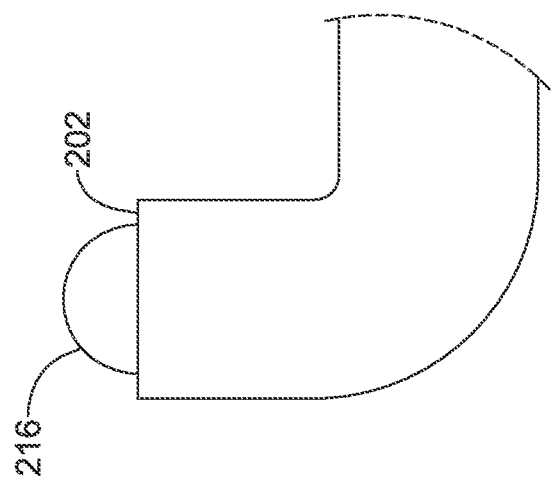
Figure 13D:
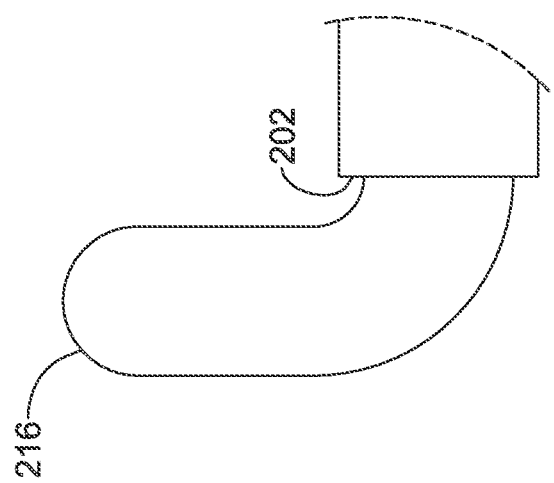

FIG. 13C shows a further advancement of the second insertion tool 216. FIG. 13D illustrates an optional next step in which the first insertion tool is advanced over the second insertion tool to bring the distal tip 202 of the first insertion tool near the distal tip 216 of the second insertion tool.

Figure 14:
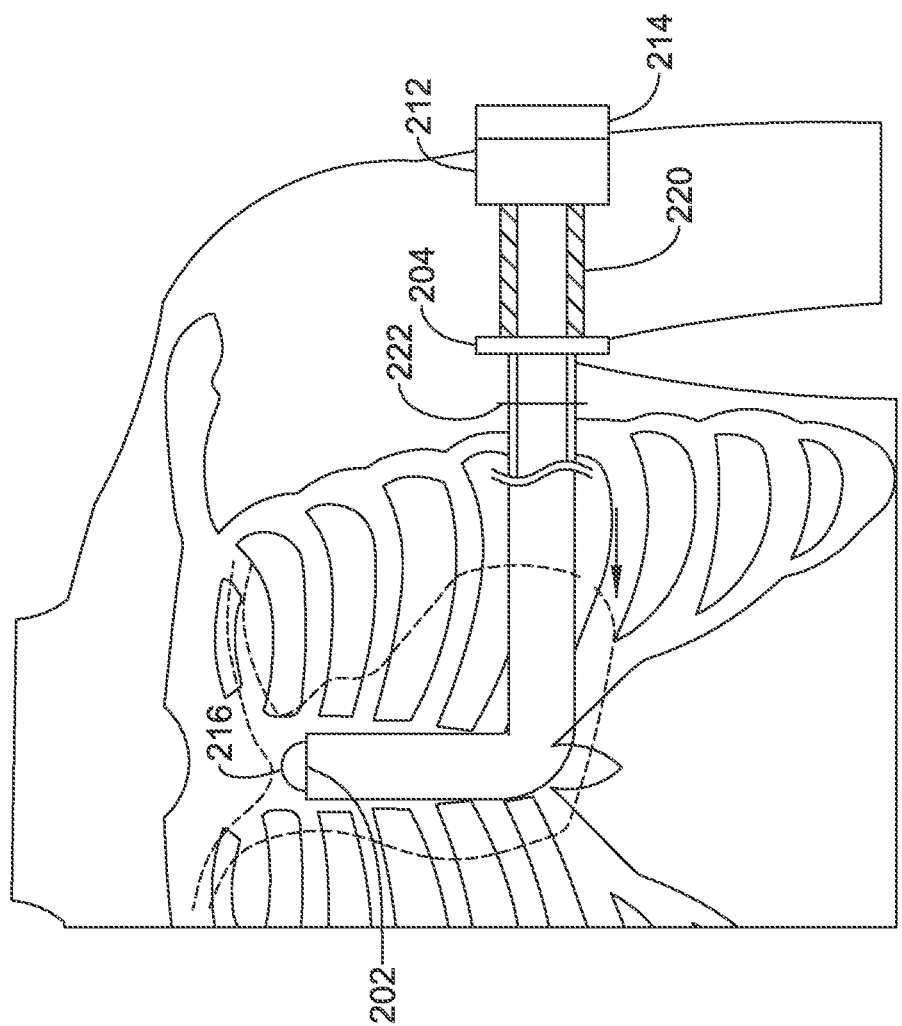

In one example, the first insertion tool is relatively flexible while the second insertion tool is pre-curved and, during the insertion step shown in FIG. 11, one or more removable stiffeners are placed in the first insertion tool—or one or more straighteners are placed in the second insertion tool— to maintain the overall combination generally straight when tunneling from the patient's left axilla to the xiphoid. After the precurved second insertion tool traverses/establishes the turn, then the stiffeners are removed from the first insertion tool to facilitate its advancement. Once the configuration of FIG. 13D is achieved and the curve of the subcutaneous tunnel is established, stiffeners can be reintroduced to facilitate continued tunneling in the parasternal direction, for example as shown in FIG. 14. In another alternative, once the turn is established and the configuration of FIG. 13D achieved, the second insertion tool may be removed and a separate dissector introduced through the first insertion tool, with the separate dissector lacking the pre-curved shape and instead being generally straight for use in dissecting the remainder of the parasternal subcutaneous tunnel.

Figure 15:
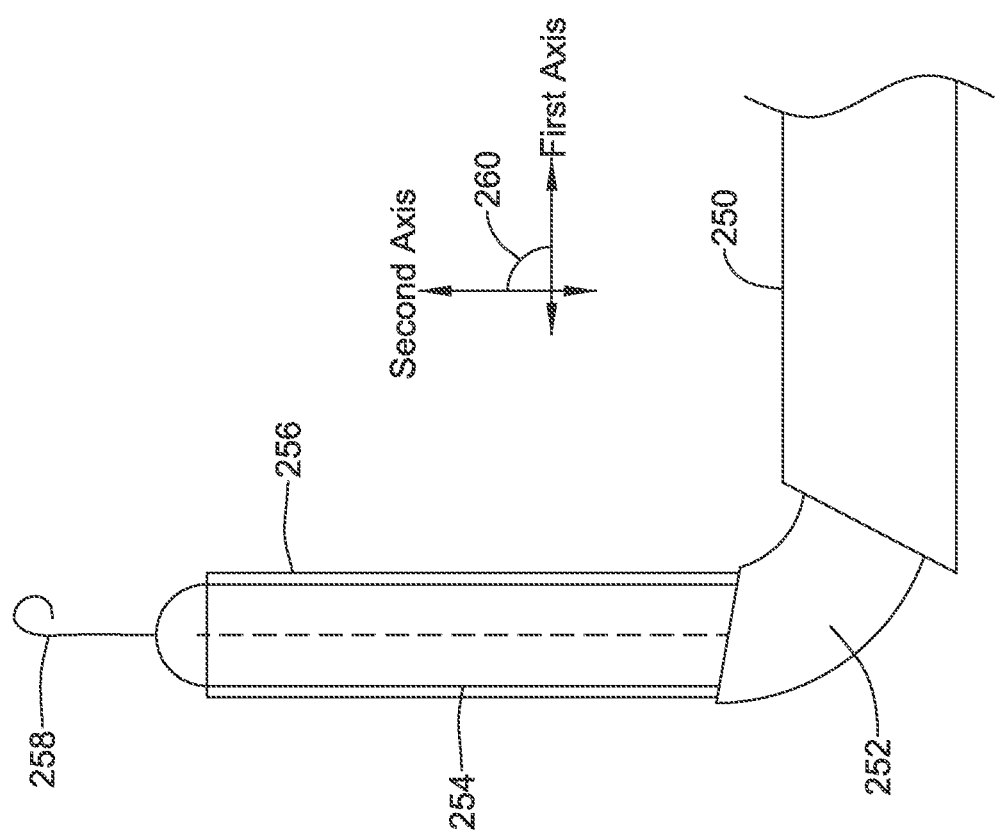
FIG. 15 shows an illustrative example using both a guidewire and a sheath.

FIG. 15 shows an illustrative example using both a guidewire and a sheath. In this illustration, a first insertion tool 250 extends within a first subcutaneous tunnel along a first axis, and a second insertion tool 252 is used to traverse an angle 260 between the first subcutaneous tunnel and a second subcutaneous tunnel that extends along a second axis. From the distal end of the second insertion tool 252, a dissector 254 extends along the second axis toward a desired location. A splittable sheath 256 is placed over the dissector during its introduction and is configured to remain in place while the dissector 254 is removed. A guidewire 258 passes through the dissector 254 and is also configured to remain in place upon removal of the dissector.

The illustration shows two ways in which an electrode can then be introduced. In one example, the dissector 254 can be removed and a lead threaded over the guidewire to the desired implant location, and the guidewire can then be removed without disturbing the lead distal tip location. In another example a lead is inserted through the splittable sheath, which can then be split at its proximal end and removed over the lead without disturbing the lead distal tip location. The first insertion tool 250 and second insertion tool 252 may remain in place during lead insertion, or one or both may be removed. In most examples only one of the splittable sheath 256 or guidewire 258 would be used, though both are shown in FIG. 15.

FIGS. 16A-16D show a cutting tool 272 at the distal end 270 of an insertion tool, with an inner dilator or dissector 276 disposed within the lumen of the insertion tool, as shown in FIG. 16A. The cutting tool 272 may extend around the insertion tool entirely, as shown, or may be provided on a lesser part of the circumference or in an angled configuration. One or more control wires 274 are connected to the cutting tool 272 to allow a user to control extension and retraction of the cutting tool 272.

FIG. 16B is a cross sectional view along line B-B of FIG. 16A. The dissector 276 is within the central lumen of the insertion tool distal end 270, and the control wire resides in a secondary lumen 278 as shown.

FIG. 16C shows another cross section, this time along line C-C of FIG. 16A. Again the dissector 276 is in the main lumen of the insertion tool, and an annular lumen is provided in which the cutting tool 272 resides at the distal end 270 of the insertion tool. This design can be achieved by having first and second outer tubes near the distal end 270 of the insertion tool and selectively laser welding the two tubes, leaving a portion unwelded, for example. In another example, an outermost tube is heat shrunk to adhere to an inner tube, with a mandrel used near a distal tip to create an annular space. In another example, the main lumen and secondary lumen are formed during an extrusion process, and the annular portion of the secondary lumen is formed in a grinding or other removal step.

FIG. 16D illustrates extension of the cutting tool 272 from the distal end 270 of the insertion tool. The cutting tool 272 can be extended beyond the distal end of the dissector 276, as shown, by manipulating the control wire 274.

FIGS. 17A-17C show another cutting tool design for an insertion tool 290. Here an inner needle or hypotube 292 is provided within the insertion tool 290. The insertion tool 290 and hypotube 292 both have a distal end with an angled face or bevel, as shown in FIG. 17A. As highlighted in FIG. 17B, the distal tip of the insertion tool 290 extends beyond the distal tip of the hypotube 292. The hypotube 292 is sharpened at its distal tip, and so the configuration shown in FIG. 17B prevents cutting during advancement within tissue. When cutting is needed, as shown in FIG. 17C, the hypotube 292 is twisted relative to the insertion tool 290, allowing the distal tip of the longer side of the angled distal end of the hypotube 292 to extend past the distal end of the insertion tool 290, facilitating a cutting action.

Figure 18:
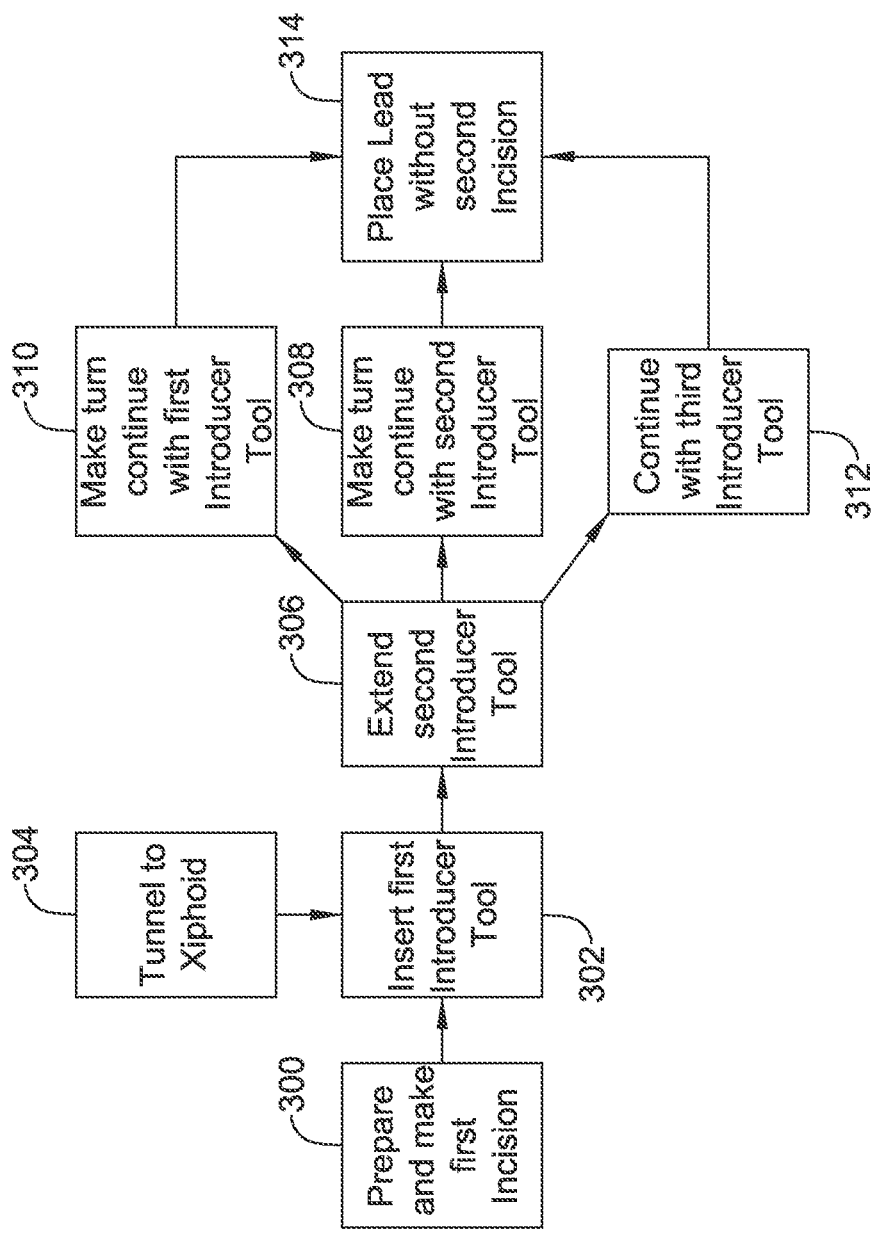
FIG. 18 is a flow diagram for various illustrative methods.

FIG. 18 is a block flow diagram for several illustrative methods. Starting at block 300, the sterile field is prepared and the first incision is made, as shown at 300. A first introducer or insertion tool is inserted as indicated at 302. Step 302 may include tunneling, in some examples, from approximately the left axilla toward the vicinity of the xiphoid (that is, to within about 5 cm, or closer, of the xiphoid) as shown at 304.

Tunneling to the vicinity of the xiphoid 304 may include tunneling from the left axilla to a location somewhat superior to and on the left side of the xiphoid. Alternatively, step 304 may include tunneling past the xiphoid by, for example, tunneling from the left axilla to the right side of the sternum to implant a patient with a right parasternal lead, in selected cases where, for example, a patient has a very centrally located heart or a small heart. For a patient having a right-sided heart or a physical limitation preventing use of the left axilla, an incision may be made at the right axilla and tunneled toward the xiphoid from there. For some physicians, particularly with smaller patients, rather than a relatively anterior left axilla implant, a deeper implant at or anterior of the left posterior axillary line may be preferred, calling for the lateral incisions shown in various Figures above to be more of a midaxillary position.

Next, a second introducer tool 306 is extended from the first introducer tool, as shown at 306. In some examples, the second introducer tool 306 is used to "make the turn".

In some examples, once the turn is made with the second introducer tool, the second introducer tool can then be used to continue to a desired target implant location, as indicated at 308. One method as summarized in block 308 is shown at FIGS. 13B-13C, where the second introducer tool can be extended from the distal tip of the first introducer tool and then extends along the second axis to the desired target implant location.

In another example summarized at block 310, a second introducer tool is used to make the turn, and the first introducer tool then follows and is advanced superiorly from the turn to the desired target implant location. One such method is shown in FIG. 14.

Another approach is to make the turn with the second introducer tool and proceed as shown in FIG. 15. For this example, the second introducer tool 252 is used to turn from the first introducer tool 250 and provides the base position for advancing a further tool, a "third introducer tool" as indicated at 312.

Any of these different approaches 308, 310, 312 may be used to achieve the final goal, which is to compete the implantation of the lead without making a second incision as indicated at 314 aside from the incision at the site of the implantable canister. As shown in several examples above, a splittable sheath or a guidewire, or both or neither, may be used to implant the lead once tunneling is completed.

In some alternative examples, the introducer 302 may take place in a manner different than block 304 suggests. For example, a first incision may be made in a high pectoral position near the clavicle on the left or right side of a patient, with introducer therefrom toward the manubrium or upper sternum. Then, "making the turn" at any of 308, 310 or 312 would direct a second tunnel inferiorly along the sternum.

While the above description focuses primarily on a subcutaneous-only implantation, tools such as those described may also be used for a substernal implantation. Substernal implantation may be achieved, for example, by tunneling from a left axillary position to a location near the xiphoid but below the lower rib margin, and proceeding superiorly along the back side of the sternum without penetrating the pericardium or lungs. In addition, rather than a subcutaneous-only implantation, the above described tools and methods may also be used to implant a subcutaneous lead for use with a cardiac device having one or more transvenous or epicardial electrodes/leads.

It may be noted that the terms introducer, introducer tool, and insertion tool may be used interchangeably herein, in general.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of implanting a subcutaneous defibrillation lead in a patient comprising:
   making a first incision;
   inserting a first insertion tool having a distal end and a proximal end via the first incision and directing the first insertion tool to a target location to establish a first subcutaneous tunnel from the incision toward the target location, the first subcutaneous tunnel extending along a first axis;
   extending a second insertion tool from within the first insertion tool, wherein the distal end of the first insertion tool lies on the first axis when the second insertion tool is extended from at or near the distal end of the first insertion tool along a second axis at an angle of at least 30 degrees from the first axis, to form at least a portion of a second subcutaneous tunnel along the second axis;
   wherein the second insertion tool comprises a proximal end with a handle and a distal end, and the step of extending the second insertion tool includes using a blunt dissector removably placed within the second insertion tool to dissect tissue, wherein the second insertion tool is used to determine the direction in which the blunt dissector is directed.

2. The method of claim 1 wherein the first insertion tool is a powered tool having an ultrasonic transducer to facilitate tunneling through tissue, and the step of inserting the first insertion tool comprises activating the ultrasonic transducer.

3. The method of claim 1 wherein the second insertion tool is steerable and includes a steering control at the proximal end thereof, and the step of extending the second insertion tool includes steering the distal end thereof in a desired direction toward the second axis.

4. The method of claim 1 wherein the second insertion tool includes a deployable cutter for facilitating advancement of the second insertion tool, and the step of extending the second insertion tool comprises using the deployable cutter to direct the second insertion tool along the second axis.

5. The method of claim 1 wherein the second axis is at an angle of about 90 degrees from the first axis.

6. The method of claim 1 wherein the first axis generally extends along a transverse plane of the patient, and the second axis generally extends along a sagittal or parasagittal plane of the patient.

7. The method of claim 1 wherein the first subcutaneous tunnel extends from approximately the left axilla toward the sternum, and the second subcutaneous tunnel extends from a location 1-5 cm left and superior to the xiphoid toward the manubrium in a direction generally parallel to the sternum.

8. The method of claim 1 wherein the blunt dissector is configured for longitudinal strength but not lateral strength.

9. The method of claim 1 wherein the second insertion tool is steerable and includes a steering control at the proximal end thereof, and the step of extending the second insertion includes steering the distal end thereof in a desired direction toward the second axis with the blunt dissector therein.

10. The method of claim 1 further comprising advancing the blunt dissector from the distal end of the second insertion tool to form the second subcutaneous tunnel such that:
the first insertion tool extends from the first incision to the target location;
the second insertion tool extends from the distal end of the first insertion tool along a curve to the start of the second subcutaneous tunnel; and
the blunt dissector extends from the start of the second subcutaneous tunnel to a distal end thereof.

11. The method of claim 10 wherein the blunt dissector is provided with a lumen therein for advancement or placement of a guidewire, and the method further comprises:
advancing the guidewire through the lumen to near or at the distal end of the second subcutaneous tunnel;
removing at least the blunt dissector while keeping the guidewire in a desired place;
advancing a lead over the guidewire to a desired lead position; and
removing the guidewire.

12. The method of claim 10 wherein the blunt dissector is provided with a lumen for advancement or placement of a guidewire, and the step of advancing the blunt dissector is performed with the guidewire contained in the lumen of the dissector and the method further comprises:
removing at least the blunt dissector over the guidewire while keeping the guidewire in a desired place;
advancing a lead over the guidewire to a desired lead position; and
removing the guidewire.

13. The method of claim 10 wherein the step of advancing the blunt dissector is performed with a tearable sheath thereover, and the method further comprises:
removing at least the blunt dissector while keeping the sheath in a desired place;
advancing a lead within the tearable sheath to a desired lead position; and
removing the tearable sheath over the lead.

14. The method of claim 1 further comprising:
advancing the second insertion tool such that a distal tip thereof is at or near a desired position;
advancing the first insertion tool over the second insertion tool such that the distal end of the first insertion tool is at or near the desired position;
removing the second insertion tool from within the first insertion tool;
inserting a lead having a proximal end and a distal end such that the distal end thereof is at or near the desired position; and
removing the first insertion tool over the lead.

15. The method of claim 14 further comprising:
anchoring the lead such that its distal end will remain at or near the desired position; and
closing the first incision such that the method is completed without making a second incision.

16. The method of claim 1 wherein the first insertion tool is generally straight.

17. The method of claim 1 wherein, when the second insertion tool exits the first insertion tool, the first insertion tool is generally straight.

* * * * *